United States Patent [19]

Slovacek et al.

[11] Patent Number: 5,242,837
[45] Date of Patent: Sep. 7, 1993

[54] METHOD FOR THE RAPID DETECTION OF ANALYTES INVOLVING SPECIFIC BINDING REACTIONS AND THE USE OF LIGHT ATTENUATING MAGNETIC PARTICLES

[76] Inventors: Rudolf E. Slovacek, 60 King St., Norfolk, Mass. 02056; Michael A. Harvey, P.O. Box 414, Spofford, N.H. 03462

[21] Appl. No.: 632,991

[22] Filed: Dec. 24, 1990

[51] Int. Cl.$^5$ .................................. G01N 33/536
[52] U.S. Cl. .................................. 436/536; 436/172; 436/524; 436/525; 436/526; 436/800; 436/538; 436/541; 436/805
[58] Field of Search .............. 435/7.92, 7.93, 7.94, 435/7.95; 436/172, 524, 525, 526, 536, 538, 541, 800, 805

[56] References Cited

U.S. PATENT DOCUMENTS

| | | | |
|---|---|---|---|
| 4,318,707 | 3/1982 | Litman et al. | 436/524 |
| 4,451,434 | 5/1984 | Hart | 436/805 |
| 4,777,145 | 10/1988 | Luotola et al. | 436/525 |

Primary Examiner—Robert J. Hill, Jr.
Assistant Examiner—Christopher L. Chin
Attorney, Agent, or Firm—Brian D. Voyce

[57] ABSTRACT

The present invention relates to an optical apparatus and a uniaxial method for rapidly measuring spectroscopically labelled specific binding analytes in a reaction assay mixture that contains unbound label without requiring the physical separation of the unbound label from the reaction mixture or sequential reagant additions and incubations. Moreover, the technique is equally applicable to measurements in either serum or whole blood.

16 Claims, 3 Drawing Sheets

METHOD FOR THE RAPID DETECTION OF ANALYTES INVOLVING SPECIFIC BINDING REACTIONS AND THE USE OF LIGHT ATTENUATING MAGNETIC PARTICLES

TECHNICAL FIELD

The present invention relates to an optical apparatus and a uniaxial method for rapidly measuring spectroscopically labelled, specific binding analytes in a reaction assay mixture that contains unbound label without requiring the physical separation of the unbound label from the reaction mixture or sequential reagent additions and incubations. Moreover, the technique is equally applicable to measurement in either serum or whole blood.

BACKGROUND ART

Current medical practice and health care policies require that clinically relevant specific binding analytes must be measured rapidly and economically. In order to perform an assay of an analyte that reacts in or with the result of a specific binding reaction, the prior art often resorted to the physical separation of the bound from the unbound labelled partner of the analyte and subsequent wash steps of the solid phase after a specific binding reaction has occurred. For example, R. Whitehead et al., in U.S. Pat. No. 4,544,088 disclose the use of collodial magnetic conjugates to separate radiolabelled antibody/antigen complexes. Other commercial embodiments use porous particles made from glass (see Bluestein et al. U.S. Pat. No. 4,780,423) or latex (see Zuk et al. U.S. Pat. No. 4,654,300). Incubation of particulate solid phase materials in liquids of high density to prevent settling and subsequent dilution to promote gravimetric settling as a method of separation was described by Baker et. al. in U.S. Pat. No. 4,656,143. In this case, dilution reduced the amount of unbound material physically associated with the settled solid phase.

In an attempt to eliminate separation and washing steps in binding assays, the art has used immiscible liquids or higher density media to keep particles suspended while a binding reaction occurs. First described in W.C. Werheiser and W. Bartley, Biochem. J. 66 pg 79 (1957), and later in M. Klingenberg and E. Pfaff, Methods in Enzymology, Vol X pg 680 (1967), and even more eloquently applied in R. McLilley et. al., Biochemica et Biophysica Acta 960 pg 259 (1977) chloroplasts are suspended in an aqueous medium over silicon oils during a $C^{14}$ uptake (binding) reaction. To separate the bound $C^{14}$ from unbound material the particulate chloroplasts were centrifuged out of the aqueous reaction medium, through the oil, and into a metabolic reaction terminating layer.

Another similar method described by W. R. Hargreaves in U.S. Pat. No. 4,868,130, describes the use of an imiscible boundary effect to separate bound from unbound labelled components in an immunological reaction mixture. The specific binding reaction occurs in a solution which is immiscible with an underlying "primary layer". The resulting labelled analyte complex is sufficiently different from the unbound label, e.g. bound to particles, such that when a force is applied to the labelled analyte complex it is drawn into the primary layer, leaving the unbound label behind in the reaction mixture. If the label is fluorescent, then Hargreaves uses side-excitation in the bottom region of the primary layer to prevent excitation of the free label in the upper aqueous layer, the detector being at a right angle thereto.

SUMMARY OF THE INVENTION

The present invention relates to a uniaxial optical method for detecting an analyte that reacts in a specific binding reaction in a solution and an apparatus therefor. The reaction uses conventional light-detectable labelling compounds. For the purposes of this disclosure, the term "specific binding analyte" refers to any relevant molecule or moiety which engages in a specific binding reaction with a complementary specific binding partner, and thus, includes antibody-antigen reactions, corresponding nucleic acid hybridization reactions, enzyme substrate binding reactions, hormonal or neural receptor binding reaction or other binding reactions involving metal and ligands or chromophores (an example of which could involve the protonation of a dye molecule). The spectroscopic labels can be detected either for their fluorescent emission properties or for their absorbance properties.

The present method involves the placement of labelled analyte complexes onto or adjacent to the surface of the optically transparent member of a sample device, to form a specific signal generating layer; the use of a light attenuating barrier on top of or as part of the labelled analyte complexes; and the detection of a signal radiation along the axis of excitation of the label. In general, the method can be practiced in four major ways. The first variant is to concentrate the labelled analyte complexes onto the surface of the optically transparent member, then to add a light attenuating barrier on top of the complexes. The second variant is to incorporate light attenuating particles or moieties into the complexes and concentrate them as in the first variant. Thus no separate barrier addition is needed. The third variant is to bind the complexes to the surface of the optically transparent member, then again add a barrier as in the first variant. Finally, the fourth variant is to bind the complexes as in the third variant, but to incorporate the light attenuating particles as in the second variant. In all variants, the sample may also comprise, in part, either naturally or by doping, light attenuating moieties (including particles or compounds) which do not become part of the labelled analyte complexes. Examples of such moieties include erythrocytes naturally found in whole blood samples or hemoglobin added as a dopant to serum samples.

With respect to the specific binding reactions the artisan can follow conventional techniques of mixing a sample having an analyte that reacts in a specific binding reaction with a complementary specific binding component system to form spectroscopically labelled or identifiable analyte complexes. Such systems are known to the art, including specific binding assay formats referred to as competitive, sandwich, or reverse sandwich assays. The mixing can occur either within or outside of a bulk sample container device described later herein. If mixed outside, the reaction mixture containing the labelled analyte complexes are placed in the sample device for measurement. In the third and fourth variants of the present method, either the labelled analyte complexes must be formed in the sample device or a subsequent reaction must take place within the sample device, in either case resulting in the complexes being bound to the surface of the optically transparent member. However, the first and second variants do not require any such reactions in the sample device. They rely upon the labelled analyte complexes having properties, such as magnetic properties or density characteristics, which enable them to be concentrated onto the surface forming a specific signal generating layer.

The spectroscopic label in all of the variants is excited by guiding an excitation radiation through the optically transparent member, onto the solution surface at such member, and into the specific signal generating layer. The signal radiation produced by this excitation returns through the optically transparent member and is detected along this axis of excitation by conventional spectroscopic means.

The present apparatus comprises an optical sample device and an optical, uniaxial excitation/detection device designed and configured to cooperate with the sample device.

The sample device comprises a bulk sample container designed and configured to receive the sample or reaction mixture and an optical detection chamber which communicates with the bulk sample container and an optically transparent member upon which labelled analyte complexes are concentrated or bound to form the specific signal generating layer. Ideally, the sample device geometry would comprise a volume greater than that of the optical detection chamber which has been designed and configured to accommodate the labelled analyte complexes only. To measure for analyte, one must distinguish between the specific signal generating layer of spectroscopically labelled analyte complexes and a non-specific signal generating layer comprised, in part, of unbound label which is disposed thereto. Depending on the method variant employed, the labelled analyte complexes may contain light attenuating moieties, in which case excitation radiation cannot penetrate into the non-specific signal generating layer. If not, then an additional signal attenuating layer is disposed between the specific signal generating layer and the non-specific generating layer.

The optical excitation means of the device is disposed adjacent to the optically transparent member and is designed and configured using conventional means known to the art to guide a electromagnetic excitation radiation through the optically transparent member and into the sample chamber as described above.

The optical detection means of the device is also disposed adjacent to the optically transparent member and is designed and configured to measure any signal radiation returning from the optical sample device along the same axis as the excitation radiation, thus the uniaxial nature of the present device.

The present method and corresponding apparatus can be used in specific binding reactions which are conventionally formatted as either competitive, sandwich, or reverse sandwich immunoassays or any ligand type binding assay. Process parameters for these reactions, such as pH, times, temperatures, or reagant concentrations, are not effected by the present device and method, and thus, are known to those of ordinary skill in the art. The method and device are equally suitable for serum or whole blood samples.

PREFERRED EMBODIMENTS

The Apparatus

Figure 1:
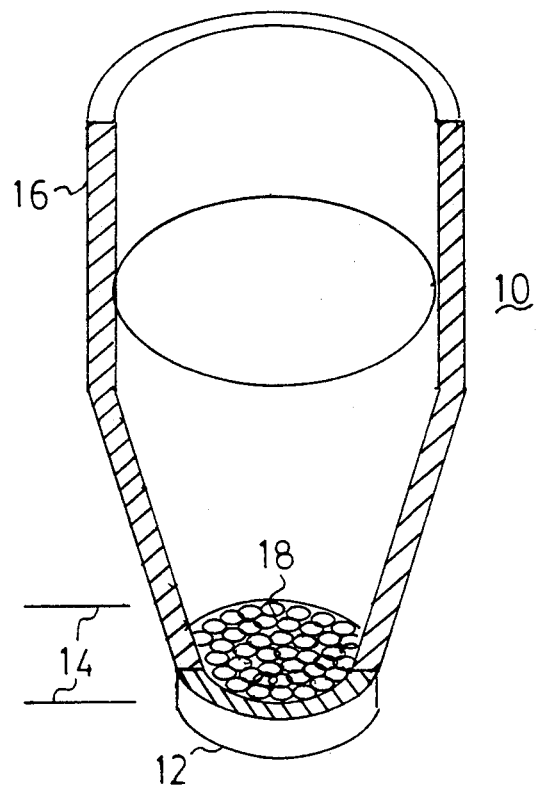
FIG. 1 is a view of the sample device.

The sample device (10) may be configured as described in FIG. 1 and duplicated in a multiwell fashion. The optically transparent members or surfaces (12) are disposed at one end of an optical detection chamber (16). These surfaces may be made of polystyrene or polymethylmethacrylate, providing approximately 100% transmission. Preferrably, the remainder of the chamber is made from an material which is not absorptive or fluorescent at exciting or signal wavelengths. The well may have any geometry including cylindrical, cubic, or frusto-conical shape. A cylindrical sample processing region which leads to a smaller frustoconical shape as in FIG. 1 would be ideal. Examples of commercially available materials which approximate this shape include the ¼ well microtiter plate configurations as made by Corning Glass Works or Costar. Nunc histocompatibility plates or Terasaki plates, as they may be called, will also work.

Where magnetic solid phase particles are used as light attenuating particles (18) within the specific binding component system, preferably, each well is in the form of an inverted frusto-conical shape. This frusto-conical shape is defined as a consequence of the selected combination of the indices of refraction through which the light is propagated, including the numerical aperture of any lenses. In addition, the configuration of the volume sampled by the optical detection means substantially equals the configuration of the volume of the optical chamber.

Figure 2:
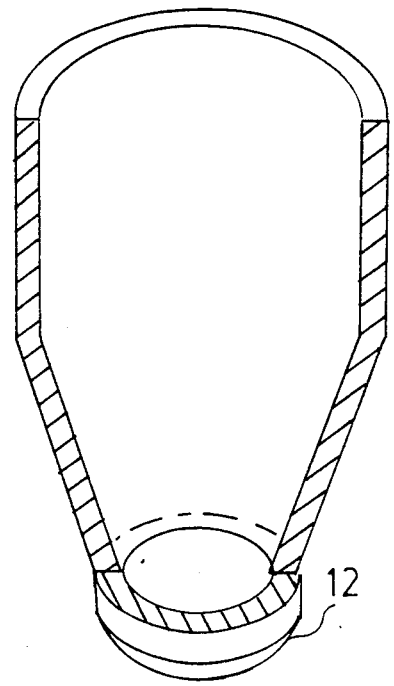
FIG. 2 is a view a preferred sample device having a lensed optical detection chamber.

Another embodiment of the present device uses an attached or molded lens (12) on the sample device (10) and is shown in FIG. 2. The optically transparent member (12) has a lens attached thereto or part thereof such that if excitation radiation is launched into the lens at a numerical aperture that is less than 0.4 with respect to an axis perpendicular to the optically transparent member, it is guided into the solution in the sample chamber (16) at a numerical aperture that is equal to or greater than 0.4.

Figure 3:
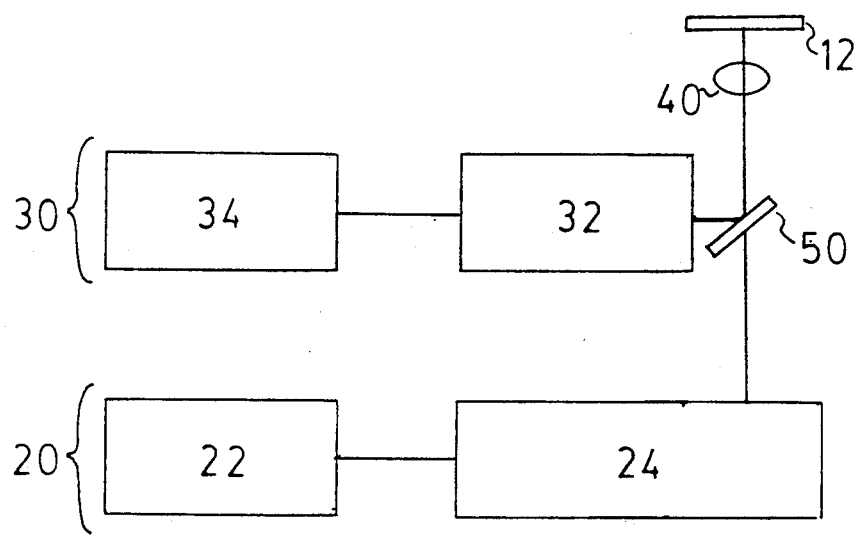
FIG. 3 is a schematic of the optical excitation and detection means suitable for the present apparatus.

A front-face fluorometric apparatus is a preferred mode to obtain measurements and is shown schematically in FIG. 3. The excitation means (30) comprises a lamp (34) and optics (32). Illumination is provided by a 10 W tungsten halogen lamp powered by a constant 6.0 v DC power supply. The filament is imaged onto a 600 micron pinhole, and the light is columnated by a set of Melles Griot aspheric lenses. An excitation wavelength of 485 nanometers is obtained by passing the beam through an Omega 485 nanometer interference filter with a 22 nanometer bandwidth. Additional color separation is provided by an Omega DC510LP beamsplitter. The pinhole image is refocused onto the bottom of the sample chamber with a 0.5 numerical aperture (NA) objective lens comprising either a conventional microscope or single element aspheric lens, producing a spot size of 510 microns and a collection angle of approximately 30°. For a selected amount of illuminating power, a smaller spot size is preferred over a larger one for a given area of optically transparent member surface.

The detection means (20) comprises optics (24) and conventional silicon photon detector (22). One should note that some elements of the launching optics are used in the detection means as well. Namely, the same lens (40) collects the signal radiation off the optical surface (12) of the chamber (16). After passing through the dichroic filter (50) and a 580 nm, 20 nm halfbandwidth interference filter, the signal is refocused by an aspherical lense onto a solid state detector (Hamamatsu S1087-01). In the case of fluorescein labels, the emission filter is replaced with a 530 nm interference filter having a half bandwidth of 30 nanometers.

In a preferred mode, the excitation radiation is launched and collected at a numerical aperture of greater than 0.4 with respect to an axis perpendicular to the optically transparent member, preferably at least 0.6 NA. If this is not easily practical, then low launch and collection NAs may be used in conjunction with the lensed device in FIG. 2.

Figure 4:
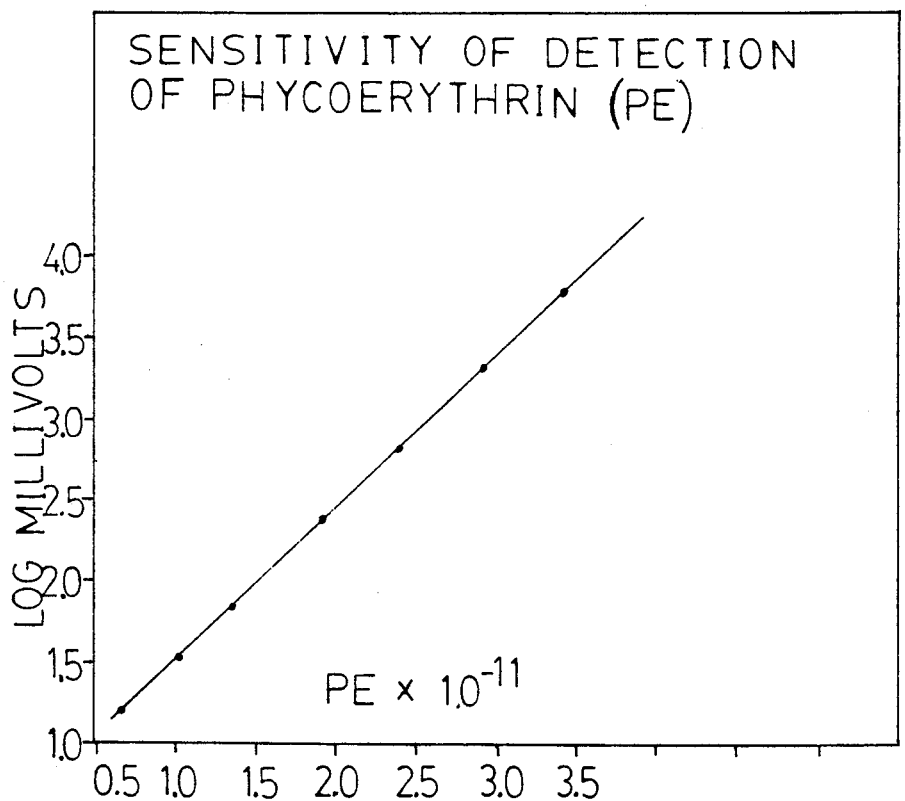
FIG. 4 is a graph of the optical response of an example of the present invention using a dilute solution of the fluorescent dye phycoerythrin.

The typical response of the above instrumentation to 100 µl samples of a dilute solution of the fluorophore phycoerythrin is displayed in FIG. 4. This graph shows that the present invention is sensitive and accurate in measuring analyte label concentrations that are within or below the levels required for clinical analytes.

The Materials and Methods

Another important embodiment adjusts the combined volume of the labelled analyte complexes and the light attenuating particles. By having the combined volumes thereof equal to or exceeding the volume of the optically sampled portion of the optical chamber, one can effectively maximize the signal that can be read, and thus, can either reduce the amount of sample required or enhance the sensitivity of the assay while simultaneously eliminating the physical removal of unreacted label from the sample chamber. If the sampled volume, in the presence of the light attenuating barrier or particles within the complexes, returns at least 90% of the theoretical amount of signal that can be generated, then there is no need to increase the amount, and hence depth (14) in FIG. 3, of the materials in the sampled volume.

Figure 5:
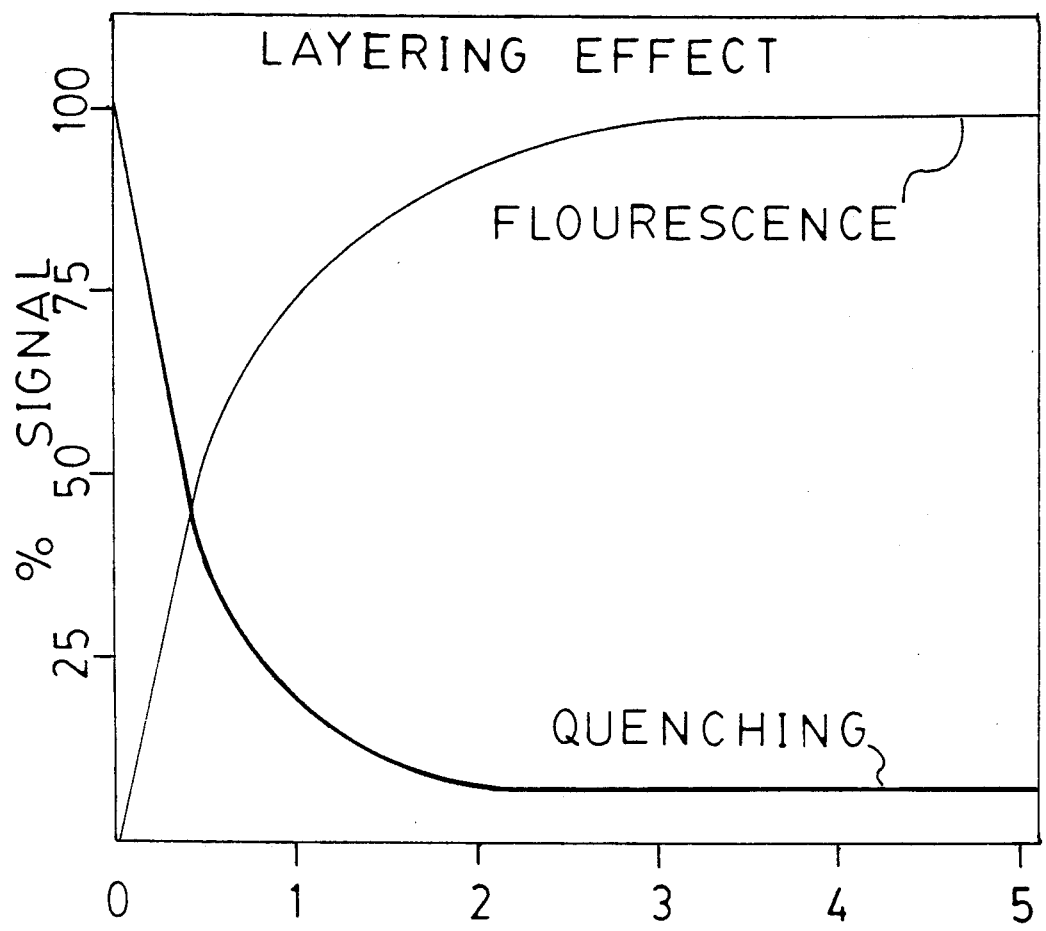
FIG. 5 is a graph illustrating the simultaneous signal generation for bound material and simultaneous light attenuation for optical isolation of freely soluble or unbound label reagent.

The particle mass required for maximum attenuation of the free unbound label signal was determined as follows. A 1% BSA- buffer was doped with fluorescein isothiocyanate (FITC) or phycoerythrin (PE) to give a fixed fluorescent value when measured in the above sample well. Unlabelled magnetic particles corresponding to a unit mass in micrograms per square mm of optical surface were added and pulled onto the well bottom prior to making a front-face measurement. As illustrated in FIG. 5, about 3.0 µg/mm² was sufficient to screen FITC or PE in solution from the excitation or detection means. To determine the maximum particale mass for optimizing the signal, particles were prepared to bind immunologically and retain a phycoerythrin labelled antibody, washed and added to the microtiter wells in increasing levels to titrate the signal increase. Once again, a mass coverage of about 3.0 µg/mm² was sufficient to give over 95% of the expected signal. On a Nunc Histocompatibility plate with a circular optical well bottom having a surface area of about 1.6 mm², this would correspond to approximately 4.8 µg in the coverage.

In terms of sample size, the optically sampled volume for a collection angle of 30° and an initial spot radius of 0.255 mm is 0.0042 mm³, which translates into about 585 ng of labelled sandwich conjugate being needed for detection. Thus only a small fraction of the particle mass used in the examples cited here is actually needed for the measurement. In fact, if the particle mass (containing excess antigen binding capacity for the assay) is raised substantially above the surface coverage needed for both attenuation and signal purposes, the signal begins to fall off even if more analyte is added. Thus, either a small shaped optical sampling volume or the shaping of the particle phase only above the optically sampled area can be used to enhance the assay sensitivity.

Also in a preferred mode, the labelled analyte complexes are moved or concentrated substantially on top of the optically transparent member before the fluorescent label is excited and a non-specific signal attenuating layer of light attenuating particles are placed above the labelled analyte complexes. Thus in the case of the reacted magnetic conjugate sandwiches, a magnetic force is applied at the bottom of the sample well so as to bring the particles onto the optical surface as depicted in FIG. 1. In the absence of a magnetic particle phase, especially in serum samples, the reaction mixture should contain enough light attenuating moeities to completely cover the surface area of the optically transparent member, thereby blocking propagation of the excitation radiation beyond the specific signal generating layer where it may encounter unreacted or unbound label in the non-specific signal generating layer.

EXAMPLES

In most of the following examples, immunoassays were performed using a sandwich format. Protein conjugated magnetic particles were used as one part of the outer layer of the sandwich while a fluorescently labelled antibody was used as the other outer layer. The collodial magnetic particles were obtained from Cortex Biochemistry of San Leandro, Calif., or Advanced Magnetics, Inc. of Cambridge, Mass. Antibodies corresponding to the desired analyte were attached to the particles in accordance with coupling procedures cited in the art (for example see Nilsson, K. and Mosbach, K. Eur. J. Biochem, 112: 397–402 (1980)). Likewise, phycobiliprotein was attached to a second set of corresponding antibodies by conventional chemical means as described in Kronick, M.N. J. Immunol. Methods 92, 1 (1986). The reaction mixture of particle conjugate, sample, and labelled antibodies were incubated as indicated.

Example 1

Goat anti-mouse antibodies form Jackson ImmunoResearch, Malvern, Pa. were coupled to paramagnetic particles obtained from Cortex. Assay mixtures composed of 20 µg of the particles with immobilized antibody, purified mouse antibody standards and 0.5 µg/ml of the phycoerythrin conjugated goat anti-mouse antibody (purchased from Biomeda of Foster City, Calif. in a 0.1% BSA PBS buffer were mixed in a volume of 100 µl and incubated for 30 min at 37° C. The paramagnetic particulate phase was separated from solution, rinsed with PBS in BSA several times then deposited on the bottom of Costar ¼ well tissue culture plate and read in the optical apparatus which as shown in FIG. 3 and described above.

The signal results shown in Table 1 clearly demonstrate that not only is a standard curve achieved, but the present assay has great sensitivity.

TABLE 1

| Concentration of Mouse Ig ($\times 10^{-12}$ Molar) | Signal (mV) |
| --- | --- |
| 5.0 | 145 |
| 10.0 | 170 |
| 20.0 | 200 |
| 40.0 | 300 |
| 80.0 | 400 |
| 160.0 | 680 |
| 320.0 | 1350 |

Example 2

Sample mixtures composed of 5 μg of magnetic particles coupled to mouse anti-CK-MM antibody, a phycoerythrin conjugated CK-MM specific antibody at 20 μg/ml, and CK-MM standards added into a total reaction volume of 100 μl were incubated for 40 min at 37° C. Sample mixture aliquots of 35 μl were then layered on 5 μl of iso-osmotic percol in Nunc histocompatibility plates. The paramagnetic particles were deposited in small spots using 3 mm diameter cobalt magnets. Fluorescent measurements were performed with an apparatus similar to that shown in FIG. 3. The results shown in Table 2 again show that the present invention has great sensitivity for a specific clinically relevant analyte, CK-MM.

TABLE 2

| ng CK-MM/ml | Relative Fluorescence |
| --- | --- |
| 1 | 15 |
| 10 | 80 |
| 20 | 150 |
| 50 | 300 |
| 100 | 1000 |
| 200 | 1500 |
| 500 | 3000 |

Example 3

A sandwich immunoassay for detecting IgE in whole blood was performed as follows. Samples (50 μl) of sheep red blood cells (SRBC) containing IgE standards at varying concentrations were added to 50 μl of a reaction medium made up with 1% BSA in a PBS buffer, goat anti-human IgE antibodies coupled to 25 μg of magnetic particles and 1 μg of BPE labelled goat anti-human IgE secondary antibody. The reaction mixtures were layered on 100 μl of iso-osmotic percol in sample wells of a Costar ½ well microtiter plate and incubated for 10 minutes at 25° C. The magnetic particles were then physically deposited on the optical surface of the microtiter wells with a series of magnets and the fluorescence signals recorded for both control and IgE containing samples.

TABLE 3

| ng IgE/ml | Relative Fluorescence |
| --- | --- |
| 15 | 22 |
| 31 | 95 |
| 62 | 155 |
| 125 | 290 |
| 250 | 600 |
| 500 | 850 |

As shown in Table 3, a linear standard curve was obtained, indicating sensitivities in the ng/ml range using an apparatus as shown in FIG. 3 and described above. Thus, the present invention can be used in an assay system for measuring analytes in whole blood samples in clinically relevant ranges. There is no need to separate the serum from the blood before analysis.

Example 4

A competitive assay for mouse Ig was constructed by first doping 50 μl of sheep red blood cells (40% by volume) with mouse Ig and 10 μg of mouse Ig immobilized on magnetic particles. An additional 50 μl of sheep red blood cells containing 5 μg/ml goat anti-mouse Ig antibodies conjugated with phycoerythrin were mixed with the standards and incubated for 40 minutes at 37° C. The reaction mixture of 100 μl was then placed on 80 μl of iso-osmotic percol in a Costar ½ well microtiter plate and the separations performed with a magnetic bar placed under a row of wells. The following table shows the results using an apparatus as shown in FIG. 3 and described above.

TABLE 4

| Mouse Ig $\times 10^{-9}$ Molar | Relative Fluorescence |
| --- | --- |
| 0.0 | 100 |
| 3.3 | 95 |
| 6.6 | 90 |
| 33.3 | 30 |
| 66.6 | 20 |

The results of Table 4 indicate that the present invention can be used to perform competitive immunoassays on serum samples in a mileau similar to whole blood.

Other embodiments of the present invention are not presented but, are obvious to those skilled in the art, and thus, are within the scope and spirit of the present invention.

We claim:

1. A method for detecting an analyte that reacts in or with the result of a specific binding reaction in a solution comprising:
   a) mixing a sample having an analyte that reacts via a specific binding reaction with a spectroscopically labelled, complementary specific binding component system to form a reaction mixture containing labelled analyte complexes, such complexes being able to be concentrated onto a surface;
   b) placing the reaction mixture with the labelled analyte complexes in a sample device, a portion of which comprises an optical detection chamber having an optically transparent member;
   c) concentrating the labelled analyte complexes onto a surface of the optically transparent member thereby forming a specific signal generating layer;
   d) placing a layer of light attenuating moieties comprised of magnetic particles between the signal generating layer and the reaction mixture by applying a magnetic force thereto, said layer covering the surface area of the signal generating layer and blocking propagation of excitation radiation into the reaction mixture;
   e) exciting the spectroscopic label by guiding an excitation radiation through the optically transparent member and into the specific generating layer, wherein the excitation radiation is launched at a numerical aperture of greater than 0.4; and
   f) measuring signal radiation from the label in the specific signal generating layer that returns through the optically transparent member, substantially along the same axis as the excitation radiation.

2. The method of claim 1 wherein the sample having an analyte and the spectroscopically labelled, complementary specific binding component system reacts to form labelled analyte complexes in the format of a competitive, sandwich, or reverse sandwich assay.

3. The method of claim 1 wherein the combined volumes of the labelled analyte complexes and the light attenuating moieties equal or exceed the volume of the optically sampled portion of the optical detection chamber.

4. The method of claim 1 wherein the sample is mixed and reacted in the optical detection chamber.

5. A method for detecting an analyte that reacts in or with the result of a specific binding reaction in a solution comprising:
   a) forming a reaction mixture by mixing a sample having an analyte that reacts via a specific binding reaction with a spectroscopically labelled, complementary specific binding component system which comprises, in part, light attenuating magnetic particles of a sufficient quantity to cover the surface area of a signal generating layer and to block propagation of excitation radiation into the reaction mixture, said system reacting to form labelled analyte complexes, said complexes being able to be concentrated onto a surface;
   b) placing the reaction mixture with the labelled analyte complexes in a sample device, a portion of which comprises an optical detection chamber having an optically transparent member;
   c) concentrating the labelled analyte complexes onto a surface of the optically transparent member thereby forming a specific signal generating layer which also blocks propagation of excitation radiation into the reaction mixture;
   d) exciting the spectroscopic label by guiding an excitation radiation through the optically transparent member and into the specific generating layer, wherein the excitation radiation is launched at a numerical aperture of greater than 0.4; and
   e) measuring signal radiation from the label in the specific signal generating layer that returns through the optically transparent member, substantially along the same axis as the excitation radiation.

6. The method of claim 5 wherein the sample having an analyte and the spectroscopically labelled, complementary specific binding component system react to form labelled analyte complexes in the format of a competitive, sandwich, or reverse sandwich assay.

7. The method of claim 5 wherein the sample also comprises additional light attenuating moeities which do not become part of the labelled analyte complexes.

8. The method of claim 5 wherein the combined volumes of the labelled analyte complexes and the light attenuating moieties equal or exceed the volume of the optically sampled portion of the optical detection chamber.

9. A method for detecting an analyte that reacts in or with the result of a specific binding reaction in a solution comprising:
   a) mixing a sample having an analyte that reacts via a specific binding reaction with a spectroscopically labelled, complementary specific binding component system thereby reacting to form a reaction mixture containing labelled analyte complexes, wherein as a result of the specific binding reaction said complexes are bound to an optically transparent member of an optical detection chamber, thereby forming a specific signal generating layer;
   b) placing a layer of light attenuating moieties comprised of magnetic particles between the signal generating layer and the reaction mixture, said layer covering the surface area of the signal generating layer and blocking propagation of excitation radiation into the reaction mixture;
   c) exciting the spectroscopic label by guiding an excitation radiation through the optically transparent member and into the specific generating layer, wherein the excitation radiation is launched at a numerical aperture of greater than 0.4; and
   d) measuring signal radiation from the label in the specific signal generating layer that returns through the optically transparent member, substantially along the same axis as the excitation radiation.

10. The method of claim 9 wherein the sample having an analyte and the spectroscopically labelled, complementary specific binding component system react to form labelled analyte complexes in the format of a competitive, sandwich, or reverse sandwich assay.

11. The method of claim 9 wherein the sample also comprises additional light attenuating particles which do not become part of the labelled analyte complexes.

12. The method of claim 9 wherein the combined volumes of the labelled analyte complexes and the light attenuating moeities equal or exceed the volume of the optically sampled portion of the optical detection chamber.

13. The method of claim 9 wherein the sample is mixed and reacted in the optical detection chamber.

14. A method for detecting an analyte that reacts in or with the result of a specific binding reaction in a solution comprising:
   a) forming a reaction mixture by mixing a sample having an analyte that reacts via a specific binding reaction with a spectroscopically labelled, complementary specific binding component system thereby reacting to form labelled analyte complexes, which, in part, are comprised of light attenuating magnetic particles of a sufficient quantity to cover the surface area of a signal generating layer and to block propagation of excitation radiation into the reaction mixture, wherein as a result of the specific binding reaction said complexes are bound to an optically transparent member of an optical detection chamber, thereby forming a specific signal generating layer which also blocks propagation of excitation radiation into the reaction mixture;
   b) exciting the spectroscopic label by guiding an excitation radiation through the optically transparent member and into the specific generating layer, wherein the excitation radiation is launched at a numerical aperture of greater than 0.4; and
   c) measuring signal radiation from the label in the specific signal generating layer that returns through the optically transparent member, substantially along the same axis as the excitation radiation.

15. The method of claim 14 wherein the sample having an analyte and the spectroscopically labelled, complementary specific binding component system react to form labelled analyte complexes in the format of a competitive, sandwich, or reverse sandwich assay.

16. The method of claim 14 wherein the combined volume of the labelled analyte complexes and the light attenuating moieties equals or exceeds the volume of the optically sampled portion of the optical detection chamber.

* * * * *